United States Patent
McCartney

(10) Patent No.: US 8,025,668 B2
(45) Date of Patent: Sep. 27, 2011

(54) MEDICAL DEVICE REMOVAL SYSTEM

(75) Inventor: Charles M. McCartney, Scottsdale, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 1694 days.

(21) Appl. No.: 11/117,790

(22) Filed: Apr. 28, 2005

(65) Prior Publication Data

US 2006/0247572 A1    Nov. 2, 2006

(51) Int. Cl.
    *A61D 1/12*    (2006.01)

(52) U.S. Cl. ........ 606/106; 600/217; 600/462; 600/463; 600/464; 600/465; 600/466; 600/467; 600/468; 600/469; 600/122; 600/200; 604/177; 604/227; 604/200; 623/1.11; 601/123; 606/79; 606/113; 606/200

(58) Field of Classification Search ................ 623/1.11; 600/217, 462–469, 122, 200; 604/177, 227, 604/200; 606/106, 79, 113, 200; 601/123

See application file for complete search history.

(56) References Cited

U.S. PATENT DOCUMENTS

| | | | | |
|---|---|---|---|---|
| 2,894,512 A | * | 7/1959 | Tapper | 606/42 |
| 3,100,489 A | * | 8/1963 | Bagley | 606/42 |
| 3,350,660 A | * | 10/1967 | Engdahl et al. | 331/65 |
| 4,004,234 A | * | 1/1977 | Juvinall | 307/652 |
| 4,041,952 A | * | 8/1977 | Morrison et al. | 606/42 |
| 4,274,413 A | * | 6/1981 | Hahn et al. | 606/42 |
| 4,425,908 A | * | 1/1984 | Simon | 128/899 |
| 4,531,287 A | * | 7/1985 | Shibata et al. | 30/43.6 |
| 4,573,994 A | * | 3/1986 | Fischell et al. | 604/891.1 |
| 4,643,184 A | | 2/1987 | Mobin-Uddin | |
| 4,655,219 A | * | 4/1987 | Petruzzi | 606/206 |
| 4,781,685 A | * | 11/1988 | Lehmann et al. | 604/117 |
| 4,784,136 A | * | 11/1988 | Klein | 606/36 |
| 4,817,600 A | | 4/1989 | Herms et al. | |
| 4,990,151 A | * | 2/1991 | Wallsten | 606/108 |
| 5,059,205 A | | 10/1991 | El-Nounou et al. | |
| 5,138,125 A | * | 8/1992 | Salesses | 219/68 |
| 5,324,304 A | * | 6/1994 | Rasmussen | 606/200 |
| 5,344,427 A | | 9/1994 | Cottenceau et al. | |
| 5,607,436 A | | 3/1997 | Pratt et al. | |
| 5,626,605 A | | 5/1997 | Irie | |
| 5,681,347 A | * | 10/1997 | Cathcart et al. | 606/200 |
| 5,685,839 A | * | 11/1997 | Edwards et al. | 604/22 |
| 5,755,790 A | | 5/1998 | Chevillon et al. | |
| 5,833,605 A | * | 11/1998 | Shah | 600/393 |
| 5,893,867 A | * | 4/1999 | Bagaoisan et al. | 606/198 |
| 5,910,144 A | * | 6/1999 | Hayashi | 606/108 |
| 5,913,874 A | * | 6/1999 | Berns et al. | 606/205 |

(Continued)

OTHER PUBLICATIONS

PCT Search Report and Written Opinion, PCT/US06/15438, Aug. 31, 2007.

(Continued)

*Primary Examiner* — Nicholas D Lucchesi
*Assistant Examiner* — Scott Medway
(74) *Attorney, Agent, or Firm* — Rutan & Tucker, LLP

(57) ABSTRACT

A medical device removal system includes a vessel filter repositioning or removal device to remove and/or reposition a medical device, such as a vessel filter. The system includes a gripper to grip a medical device that is located within a body vessel, and a detector, linked to the gripper, to detect the proximity of the medical device to the gripper. The system may also include an output to indicate a signal from the detector.

12 Claims, 3 Drawing Sheets

U.S. PATENT DOCUMENTS

| | | | |
|---|---|---|---|
| 5,989,242 A * | 11/1999 | Saadat et al. | 606/1 |
| 6,033,402 A * | 3/2000 | Tu et al. | 606/41 |
| 6,068,645 A * | 5/2000 | Tu | 606/200 |
| 6,086,586 A * | 7/2000 | Hooven | 606/50 |
| 6,102,917 A * | 8/2000 | Maitland et al. | 606/108 |
| 6,109,852 A * | 8/2000 | Shahinpoor et al. | 414/1 |
| 6,156,055 A * | 12/2000 | Ravenscroft | 606/206 |
| 6,187,016 B1 * | 2/2001 | Hedges et al. | 606/108 |
| 6,200,280 B1 * | 3/2001 | Brenneman et al. | 601/41 |
| 6,217,585 B1 * | 4/2001 | Houser et al. | 606/108 |
| 6,258,026 B1 | 7/2001 | Ravenscroft | |
| 6,273,901 B1 * | 8/2001 | Whitcher et al. | 606/200 |
| 6,277,125 B1 * | 8/2001 | Barry et al. | 606/108 |
| 6,342,062 B1 * | 1/2002 | Suon et al. | 606/200 |
| 6,348,862 B1 * | 2/2002 | McDonnell et al. | 340/562 |
| 6,383,198 B1 * | 5/2002 | Hamilton | 606/115 |
| 6,443,972 B1 | 9/2002 | Bosma et al. | |
| 6,447,530 B1 | 9/2002 | Ostrovsky et al. | |
| 6,471,659 B2 * | 10/2002 | Eggers et al. | 600/564 |
| 6,478,773 B1 * | 11/2002 | Gandhi et al. | 604/113 |
| 6,497,709 B1 | 12/2002 | Heath | |
| 6,506,205 B2 | 1/2003 | Goldberg et al. | |
| 6,508,825 B1 * | 1/2003 | Selmon et al. | 606/198 |
| 6,517,559 B1 | 2/2003 | O'Connell | |
| 6,540,767 B1 | 4/2003 | Walak et al. | |
| 6,558,376 B2 * | 5/2003 | Bishop | 606/27 |
| 6,569,160 B1 * | 5/2003 | Goldin et al. | 606/41 |
| 6,575,965 B1 * | 6/2003 | Fitch et al. | 606/15 |
| 6,605,102 B1 * | 8/2003 | Mazzocchi et al. | 606/200 |
| 6,620,183 B2 | 9/2003 | DiMatteo | |
| 6,676,660 B2 * | 1/2004 | Wampler et al. | 606/51 |
| 6,726,703 B2 * | 4/2004 | Broome et al. | 606/200 |
| 6,846,317 B1 | 1/2005 | Nigon | |
| 6,872,217 B2 * | 3/2005 | Walak et al. | 606/200 |
| 6,911,037 B2 * | 6/2005 | Gainor et al. | 606/213 |
| 6,918,880 B2 * | 7/2005 | Brookner et al. | 600/565 |
| 6,918,919 B2 * | 7/2005 | Krag | 606/185 |
| 6,941,169 B2 * | 9/2005 | Pappu | 607/9 |
| 6,949,103 B2 * | 9/2005 | Mazzocchi et al. | 606/108 |
| 6,953,473 B2 * | 10/2005 | Porter | 606/213 |
| 7,001,424 B2 | 2/2006 | Patel et al. | |
| 7,033,376 B2 | 4/2006 | Tsukernik | |
| 7,041,117 B2 | 5/2006 | Suon et al. | |
| 7,063,707 B2 * | 6/2006 | Bose et al. | 606/127 |
| 7,097,643 B2 * | 8/2006 | Cornelius et al. | 606/32 |
| 7,144,408 B2 * | 12/2006 | Keegan et al. | 606/200 |
| 7,147,649 B2 | 12/2006 | Thomas | |
| 7,166,106 B2 * | 1/2007 | Bartel et al. | 606/51 |
| 7,169,172 B2 * | 1/2007 | Levine et al. | 623/1.11 |
| 7,214,237 B2 * | 5/2007 | Don Michael et al. | 606/200 |
| 7,323,003 B2 * | 1/2008 | Lowe | 606/200 |
| 7,347,843 B2 * | 3/2008 | Adams et al. | 604/288.02 |
| 7,357,809 B2 * | 4/2008 | Jones et al. | 606/205 |
| 7,367,985 B2 * | 5/2008 | Mazzocchi et al. | 606/200 |
| 2001/0000799 A1 | 5/2001 | Wessman et al. | |
| 2002/0138097 A1 | 9/2002 | Ostrovsky et al. | |
| 2002/0193828 A1 | 12/2002 | Griffin et al. | |
| 2003/0199918 A1 | 10/2003 | Patel et al. | |
| 2003/0208227 A1 | 11/2003 | Thomas | |
| 2003/0208253 A1 | 11/2003 | Beyer et al. | |
| 2004/0102806 A1 | 5/2004 | Broome et al. | |
| 2004/0210121 A1 * | 10/2004 | Fuimaono et al. | 600/374 |
| 2005/0251197 A1 * | 11/2005 | Hensley et al. | 606/200 |
| 2005/0288703 A1 | 12/2005 | Beyer et al. | |
| 2005/0288704 A1 | 12/2005 | Cartier et al. | |
| 2006/0004402 A1 | 1/2006 | Voeller et al. | |
| 2006/0015136 A1 * | 1/2006 | Besselink | 606/200 |
| 2006/0015137 A1 | 1/2006 | WasDyke et al. | |
| 2006/0036279 A1 | 2/2006 | Eidenschink et al. | |
| 2006/0041271 A1 | 2/2006 | Bosma et al. | |
| 2006/0069405 A1 | 3/2006 | Schaeffer et al. | |
| 2006/0069406 A1 | 3/2006 | Hendriksen et al. | |
| 2006/0079928 A1 | 4/2006 | Cartier et al. | |
| 2006/0079930 A1 | 4/2006 | McGuckin, Jr. et al. | |
| 2006/0095068 A1 | 5/2006 | WasDyke et al. | |
| 2006/0178695 A1 * | 8/2006 | Decant et al. | 606/200 |
| 2006/0203769 A1 | 9/2006 | Saholt et al. | |
| 2006/0206138 A1 | 9/2006 | Eidenschink | |
| 2006/0259067 A1 | 11/2006 | Welch et al. | |
| 2006/0259068 A1 | 11/2006 | Eidenschink | |
| 2007/0005095 A1 | 1/2007 | Osborne et al. | |
| 2007/0005104 A1 | 1/2007 | Kusleika et al. | |
| 2007/0005105 A1 | 1/2007 | Kusleika et al. | |

OTHER PUBLICATIONS

"Recovery Cone Removal System for Use With the Recovery Filter", Bard Peripheral Vascular, Inc., 2003.

"Recovery Filter System for Use in the Vena Cava", Bard Peripheral Vascular, Inc., 2003.

* cited by examiner

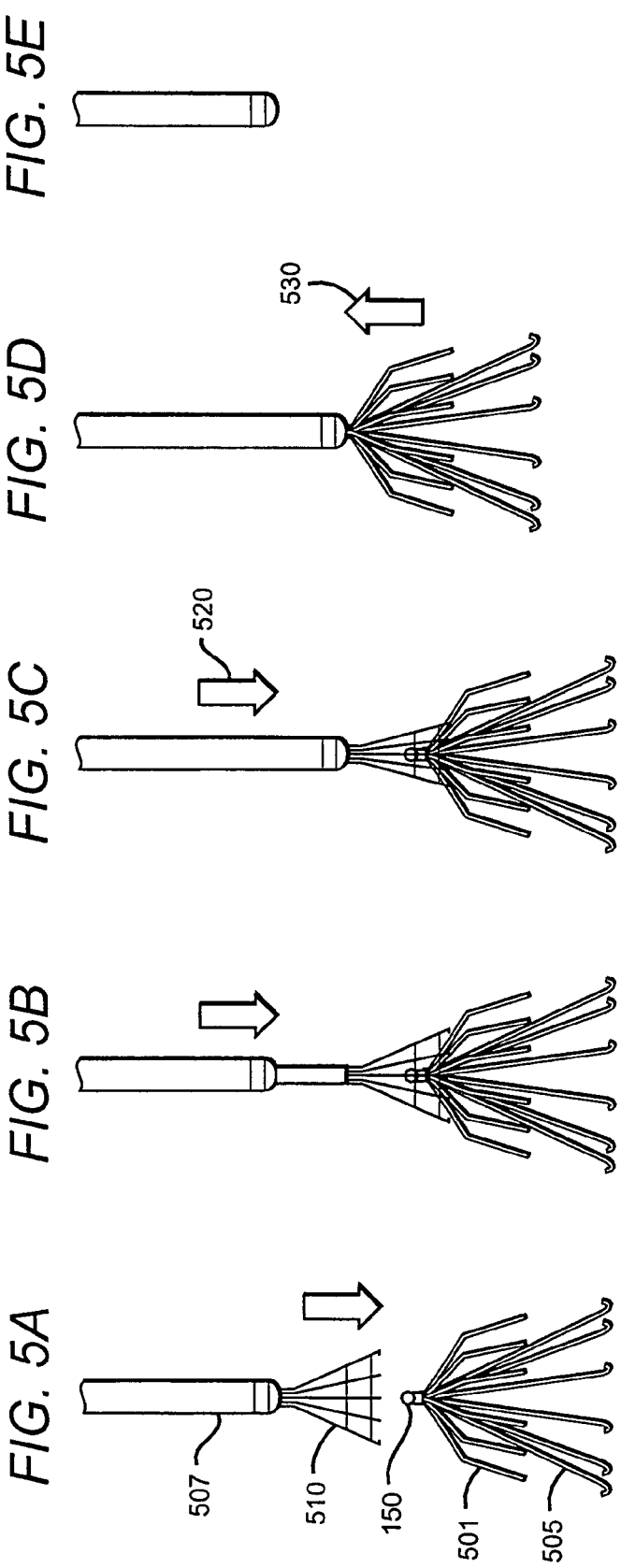

MEDICAL DEVICE REMOVAL SYSTEM

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

A vessel filter is a device inserted into a blood vessel to capture particles in the blood flow. The device may be inserted into a major vein (e.g., inferior vena cava) to prevent a blood clot from reaching the lungs. Subjects that have recently suffered from trauma, or have had a heart attack (myocardial infarction), or who have experienced a major surgical procedure (e.g., surgical repair of a fractured hip, etc.) may have thrombosis in a deep vein. When the thrombus clot loosens from the site of formation and travels to the lung it can cause pulmonary embolism, which is a life-threatening condition. To prevent pulmonary embolism and other adverse conditions that may arise due to the movement of thrombus clots, a vessel filter, such as a vena cava filter, is placed into the circulatory system to intercept the thrombi and prevent them from entering the lungs. Further, it may be useful to remove or reposition implanted vessel filters.

Examples of various blood vessel filters are disclosed in U.S. Patent Application, Publication No. 2001/0000799 A1, titled "BODY VESSEL FILTER" by Wessman et al., published May 3, 2001; U.S. Patent Application, Publication No. 2002/0138097 A1, titled "ATRAUMATIC ANCHORING AND DISENGAGEMENT MECHANISM FOR PERMANENT IMPLANT DEVICE" by Ostrovsky et al., published Sep. 26, 2002; U.S. Patent Application, Publication No. 2002/0193828 A1, titled "ENDOVASCULAR FILTER" by Griffin et al., published Dec. 19, 2002; U.S. Patent Application, Publication No. 2003/0199918 A1, titled "CONVERTIBLE BLOOD CLOT FILTER" by Patel et al., published Oct. 23, 2003; U.S. Patent Application, Publication No. 2003/0208227 A1, titled "TEMPORARY VASCULAR FILTERS AND METHODS" by Thomas, published Nov. 6, 2003; U.S. Patent Application, Publication No. 2003/0208253 A1, titled "BLOOD CLOT FILTER" by Beyer et al., published Nov. 6, 2003; U.S. Pat. No. 4,425,908, titled "BLOOD CLOT FILTER" issued to Simon, dated Jan. 17, 1984; U.S. Pat. No. 4,643,184, titled "EMBOLUS TRAP" issued to Mobin-Uddin, dated Feb. 17, 1987; U.S. Pat. No. 4,817,600, titled "IMPLANT FILTER" issued to Herms et al., dated Apr. 4, 1989; U.S. Pat. No. 5,059,205, titled "PERCUTANEOUS ANTI-MIGRATION VENA CAVA FILTER" issued to El-Nounou et al., dated Oct. 22, 1991; U.S. Pat. No. 5,344,427, entitled "FILTER WITH TRIANGULAR FINGERS" issued to Cottenceau et al., dated Sep. 6, 1994; U.S. Pat. No. 5,626,605, entitled "THROMBOSIS FILTER" issued to Irie et al., dated May 6, 1007; U.S. Pat. No. 5,755,790, titled "INTRALUMINAL MEDICAL DEVICE" issued to Chevillion et al., dated May 26, 1998; U.S. Pat. No. 6,258,026 B1, titled "REMOVABLE EMBOLUS BLOOD CLOT FILTER AND FILTER DELIVERY UNIT" issued to Ravenscroft et al., dated Jul. 10, 2001; U.S. Pat. No. 6,443,972 B1, titled "VASCULAR FILTER" issued to Bosman et al., dated Sep. 3, 2002; U.S. Pat. No. 6,497,709 B1, titled "METAL MEDICAL DEVICE" issued to Heath, dated Dec. 24, 2002; U.S. Pat. No. 6,506,205 B2, titled "BLOOD CLOT FILTERING SYSTEM" issued to Goldberg et al., dated Jan. 14, 2003; and U.S. Pat. No. 6,517,559 B1, titled "BLOOD FILTER AND METHOD FOR TREATING VASCULAR DISEASE" issued to O'Connell, dated Feb. 11, 2003; U.S. Pat. No. 6,540,767 B1, titled "RECOILABLE THROMBOSIS FILTERING DEVICE AND METHOD" issued to Walak et al., dated Apr. 1, 2003, U.S. Pat. No. 6,620,183 B2, titled "THROMBOSUS FILTER WITH BREAK-AWAY ANCHOR MEMBERS" issued to DiMatteo, dated Sep. 16, 2003; each of which is incorporated herein by reference in its entirety.

Vessel filters may be permanently inserted into a blood vessel, or they may be temporarily (or removably) inserted. Removal of a vessel filter may include repositioning a vessel filter within a blood vessel after it has been inserted, or completely removing the vessel filter from the body of a subject into whom the vessel filter was inserted. A vessel filter removal or repositioning device may be used to engage and remove a vessel filter. An example of a vessel filter removal or repositioning device is found in U.S. Pat. No. 6,156,055, titled "GRIPPING DEVICE FOR IMPLANTING, REPOSITIONING, OR EXTRACTING AN OBJECT WITHIN A BODY VESSEL" issued to Ravenscroft, which is herein incorporated by reference in its entirety.

One type of vessel filter comprises a plurality of radially expandable legs that support one or more filter baskets that are conical in configuration. Such device is adapted for compression into a small size to facilitate delivery into a vascular passageway and is subsequently expanded to contact the inner wall of a body vessel. The device may be retrieved from the deployed site by compressing the radially expanded legs and the associated baskets into a compacted size for retrieval. The radially expandable legs generally also comprise engagements for anchoring the filter in position within a vessel (e.g., the vena cava). For example, the expandable legs may have hooks that can penetrate into the vessel wall and positively prevent migration of the filter in either direction along the length of the vessel. The body of such a filter is usually formed from biocompatible materials, including compressible spring metals and shape memory materials, to allow easy expansion and compression of the filter within the vessel. The hooks on the radially expandable legs may further comprise materials more elastic than the legs to permit the hooks to straighten in response to withdrawal forces and to facilitate withdrawal from the endothelium layer without risk of significant injury to the vessel wall. In one variation, the hooks are formed on the ends of a portion of the radially expandable legs, but not on others. Of course, there are many different configurations for a vessel filter, of which the above-described vessel filter is one example.

A vessel filter may be implanted in the subject's vena cava for some period (e.g., a few weeks), after which the vessel filter may be removed. During the time of implantation, the vessel filter will usually be monitored to confirm its position and condition. For example, to verify that the vessel filter has not migrated along the length of the blood vessel or become misaligned post-implantation, complex imaging systems such as MRI, CT Scan or X-ray are used to determine the condition and/or position of the vessel filter. In some versions, the implanted vessel filter contains on-board sensors or telemetry to monitor the conditions of the filter or the vessel into which the filter is implanted. In any case, monitoring may indicate when the filter may need to be removed or repositioned. The accumulation of thrombus material may result in complications that require intervention by a physician. For example, when too much thrombus material has been trapped inside and/or behind the vessel filter, the build-up may impede blood flow in the blood vessel. The pressure build-up due to the partial blockage of the blood flow may also lead to expansion of the blood vessel, which can cause tilting and/or migration of the vessel filter.

Removal or repositioning of a vessel filter may be done in a minimally invasive way, in order to reduce trauma to a subject in need of removal or repositioning of a vessel filter. For example, a vessel filter may be endoscopically removed or repositioned. However, it may be difficult to non-invasively remove a vessel filter, because it may be difficult to determine when a vessel filter is near enough to a vessel filter repositioning or removal device for the removal device to engage the vessel filter. Thus, in most instances, removal of vessel filters from a body vessel requires complex and/or expensive visualization procedures, such as MRI, X-Ray, etc.

BRIEF SUMMARY OF THE INVENTION

Accordingly, described herein is a vessel filter repositioning or removal device having a detector that detects the proximity of a vessel filter with respect to the vessel filter repositioning or removal device.

Vessel filter repositioning or removal devices may comprise a gripper to grip a vessel filter within a body vessel and a detector, linked to the gripper, to detect the proximity of a vessel filter to the gripper. The vessel filter repositioning or removal devices may also include an output to indicate a signal from the detector. The output may comprise a light emitting diode (hereinafter "LED"), a buzzer or other visual or audio aids known to one of skill in the art. The vessel filter repositioning or removal device may also include a battery to power the detector.

In one embodiment, the detector comprises an electrical detector, wherein the electrical detector comprises a positive electrode and a negative electrode. The positive electrode and the negative electrode are configured so that contact with a vessel filter completes an electrical circuit between the positive electrode and the negative electrode. In another embodiment, the detector comprises a mechanical detector configured to signal contact with a vessel filter, or a magnetic detector, or an optical sensor. In some versions, the detector comprises a pressure detector to signal contact with a vessel filter, or a magnetic detector to detect metal from the vessel filter, or an optical sensor to detect a vessel filter entering the gripper region (e.g., a collapsible cone gripper), or a signal sensor to sense a signal from the vessel filter.

In one embodiment, the gripper comprises a collapsible cone, which comprises an elongate support body having a central longitudinal axis, a plurality of gripping members at the distal end of the elongate support body extending therefrom, wherein the gripping members are convertible between an expanded configuration, in which the gripper members extend from the central longitudinal axis, and a collapsed configuration, in which the gripping members are positioned closer to the longitudinal axis of the support body. In one embodiment, the gripper includes a flexible liner connected to the gripping members forming an inner surface. In some versions, the gripper comprises a snare.

In another embodiment, the vessel filter removal or repositioning devices comprises an elongate support body having a central longitudinal axis, a collapsible cone gripper attached to the distal end of the support body, wherein the cone is translatable between an expanded configuration and a retracted configuration, a detector linked to the gripper to detect the proximity of a vessel filter to the gripper and an output to indicate a signal from the detector.

In another embodiment, the vessel filter removal or repositioning device may include an elongate support body having a central longitudinal axis, a plurality of gripping members at the distal end of the elongate support body extending therefrom, wherein the gripping members are convertible between an expanded funnel-shaped configuration, in which the gripping members extend from the central longitudinal axis, and a retracted configuration, in which the gripping members are positioned closer to the longitudinal axis, a flexible liner connected to the gripping members forming an inner surface, and a positive electrode and a negative electrode, each in electrical connection to an output, wherein the output is configured to indicate when a vessel filter contacts the positive and negative electrodes, thereby completing an electrical circuit between the positive and negative electrodes.

At least one of the gripping members may include a hook member formed from an elongate metallic material. At least one of the gripping members may be a positive or negative electrode (e.g., as part of the detector). The positive or negative electrode may comprise a wire surrounded by the gripping members. In some versions, the positive electrode comprises a loop of electrically conductive material encircling the central longitudinal axis. In some versions, the negative electrode comprises a cup region surrounded by the gripping members. The vessel filter removal or repositioning device may also include a battery in electrical contact with the positive and negative electrodes.

Also described herein, are kits for repositioning or removing a vessel filter. A kit may include a vessel filter removal or repositioning device and instructions for using the vessel filter removal or repositioning device to remove or to reposition a vessel filter. The instructions may include a description of a method or methods of repositioning or removing a vessel filter, as described herein.

Also described herein are methods of repositioning or removing a vessel filter. One method comprises inserting a vessel filter removal or repositioning device into a body vessel containing a vessel filter, where the vessel filter removal or repositioning device comprises a gripper to remove or reposition a vessel filter from a body vessel, a detector linked to the gripper to detect the proximity of a vessel filter to the gripper, and an output to indicate a signal from the detector, approaching the vessel filter within the body vessel with the vessel filter removal or repositioning device, detecting the vessel filter with the vessel filter removal or repositioning device and gripping the vessel filter with the vessel filter removal or repositioning device.

These and other embodiments, features, and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIGS. 5A-5E illustrate removal of a vessel filter using a vessel filter removal or repositioning according to the present invention.

DETAILED DESCRIPTION OF THE INVENTION

Figure 1:
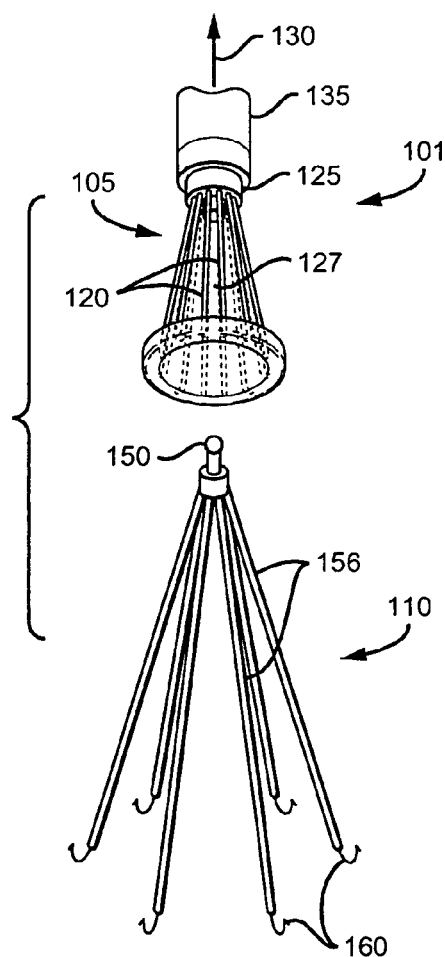
FIG. 1 shows a perspective view of a vessel filter removal or repositioning device approaching a vessel filter.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated, this invention need not be limited to applications in humans. As one of skill in the art would appreciate, variations of the invention may be applied to other mammals as well. Moreover, it should be understood that embodiments of the present invention may be applied in combination with various catheters, tubing introducers or other medical device deployment devices for implantation and/or retrieval of the filter in a vessel within a subject's body.

Vessel filter repositioning or removal devices (hereafter referred to as "removal devices") may be used to remove any appropriate object (e.g., vessel filter) from a body vessel. It should be noted that although the removal devices described here are described as removing or repositioning vessel filter devices, any appropriate medical device could be removed or repositioned using the removal devices described herein. In particular, the removal devices described herein may be used with medical devices inserted into body vessels or chambers. One example of a medical device that may be removed with the removal devices described herein are vena cava filters. However, the vena cava filters described herein are merely illustrative and are not intended to be limiting. In light of the disclosure herein, one of skill in the art would appreciate that variations of the removal devices described may be applicable for placement, repositioning or removal of any appropriate device in various hollow body organs and elongated cavities in a human body. Thus, the removal devices should not be limited to removal of vessel filters.

It must also be noted that, as used in this specification and the appended claims, the singular forms "a," "an" and "the" include plural referents unless the context clearly dictates otherwise. Thus, for example, the term "a hook" is intended to mean a single hook or a combination of hooks, "a fluid" is intended to mean one or more fluids, or a mixture thereof.

The removal devices described herein may include a gripper, to grip a vessel filter within a body, and a detector linked to the gripper to detect the proximity of a vessel filter with respect to the gripper. The detector is typically connected to an output (e.g., a visual output, aural output, electronic output, mechanical output, etc.) for indicating how near the vessel filter is to the removal device and/or whether the vessel filter is properly positioned within the gripper for engagement thereof.

Gripper

Any appropriate gripper may be used as part of the removal device to grasp and hold a vessel filter. In general, the gripper may secure (e.g., by grasping) a vessel filter so that it may be removed or repositioned. The gripper may releasably secure the vessel filter to the removal device. The gripper may also facilitate collapsing of a vessel filter, or a region of a vessel filter (e.g., collapsing the expanded legs or attachment regions of the vessel filter), so that the vessel filter may be manipulated without harming the subject (e.g., without damaging the walls of the body vessel into which the vessel filter has been placed). Examples of appropriate grippers are illustrated below and include collapsible cones and snares; however, other grippers may also be used.

FIG. 1 illustrates one example of a gripper 101 shown in a perspective view as it approaches a vessel filter 110. The gripper 101 comprises a collapsible cone region 105 formed by a plurality of gripping members 120. The collapsible cone region is attached to the distal end of an elongate support body 125 having a central, longitudinal axis 130. The cone region includes a flexible liner 127. The gripping members 120 extend approximately axially from the distal end of the elongate support body 125, and form a gripper having at least two configurations, including an expanded configuration, in which the gripping members 120 project at an angle from the central longitudinal axis of the support body to form a cone 105 (as shown in FIG. 1 and a collapsed configuration, in which the gripping members converge toward the central longitudinal of the support body (not shown). The gripping members 120 shown in FIG. 1 are flexible wires that are mounted so that their relaxed position is the "expanded" configuration, forming a cone centered about the central longitudinal axis 130 of the support body. In the embodiment shown, the gripper 101 includes an outer sleeve 135 that slides over the elongate support body and the plurality of gripping members 120, thereby collapsing the gripping members into the second, collapsed configuration.

Grippers, and particularly gripper members, may be comprised of any appropriate material, including, but not limited to, metals (e.g., aluminum, steel, tin, alloys, etc.), polymers (e.g., plastics, rubbers, etc.) and combinations thereof. Shape memory materials (e.g., nitinol), or materials that may be elastically displaced (and returned to an initial configuration) may be particularly useful in forming the gripper due to the inherent characteristics thereof. Of course, other materials not specifically mentioned herein are also suitable for forming the gripper members.

Flexible liner 127 may be connected to the gripping members as part of a funnel-shaped gripper at the distal end of the removal device. The liner may be flexible and may be attached to the gripping members on the inside of the cone region (e.g., the side for gripping the vessel filter) or on the outside of the cone region, or both. The liner may comprise multiple layers. Furthermore, the liner may be made with any appropriate material, including materials with electrical or tactile properties. For example, the liner may be comprised of electrically insulative and/or conductive regions. In some versions, the flexible liner comprises a polymeric (e.g., plastic or rubber) material. The flexible liner may cover all of the gripping members, or only a subset of the gripping members. In some versions, the flexible liner may include surface properties useful to grip (and or collapse) a vessel filter. For example, the flexible liner may include a textured surface, such as a ridged pattern, or may comprise a sticky outer coating (e.g., including an adhesive).

The elongate support body 125 may be used to position the gripper (e.g., the collapsible cone region of the gripper). In some versions, the elongate support body 125 is used to help guide the removal device to a body location (e.g., within a body vessel) by using catheter guidance techniques. For example, a guidewire or introducer may be used. Thus, in some versions, the elongate support body is structured so that it may be used with a guidewire or introducer. For example, the elongate support body may include one or more cavities (e.g., lumen or passageways). A lumen though the support body may be used to pass a guidewire, or to pass additional devices or attachments (e.g., connections) to devices at the distal end of the support body. The elongate support body may be made of any appropriate material. For example, the elongate support body may comprise a flexible material (e.g., polymers including polyurethane, etc.).

The collapsible cone portion 105 of the gripper shown in FIG. 1 is hollow, so that it may fit over at least one end of a vessel filter 110. The removal device may be used with any appropriate vessel filter, such as vessel filter 110. The vessel filter shown in FIG. 1 has a hub 150, from which a plurality of legs 155 radially project. Each arm shown in FIG. 1 has a barb or hook 160 at its end to anchor to the walls of a vessel into which the vessel filter is implanted. Thus, the hub portion 150 and a portion of the legs 155 may fit within a portion of the gripper (e.g., the collapsible cone), so that the gripper can grasp the vessel filter 110.

The gripper may also have additional structure to grasp and/or collapse the vessel filter. For example, the distal ends of at least some of the gripping members 120 may include hooks or pusher regions. Thus, in some versions, when the gripping members are converted from an expanded (cone) configuration to a collapsed (or retracted) configuration, any portion of the vessel filter within the cavity of the cone region may be trapped within the cone region. Collapsing the cone region of the gripper may also cause the legs of a vessel filter to collapse. Collapsing the vessel filter may prevent injury and facilitate removal or repositioning of the vessel filter. In some versions, the gripper region may secure the filter device without collapsing it.

Another example of a mechanical gripper that may be used includes a snare. For example, a snare in conjunction with a sleeve, may comprise a loop of material that may constrict to grasp a vessel filter. A snare may also be used to collapse (e.g., the legs) a vessel filter.

As described above, a gripper of a removal device may grasp (or otherwise secure, hold, or attach to) a vessel filter. The gripper may secure a vessel filter removably or permanently. The gripper may secure any appropriate portion or region of a vessel filter. For example, in some versions, the gripper attaches to the hub 150 of a vessel filter. In some versions, the gripper attaches to the interface between the hub and the legs. In some versions, the gripper attaches to the legs 155. The gripper may attach to multiple sites on a vessel filter, or it may attach to dedicated sites on a vessel filter (e.g., sites intended specifically for attachment to a gripper or removal device).

Although the majority of the examples described herein show grippers that mechanically grasp on to a vessel filter to secure the vessel filter, it should be understood that a gripper may secure a vessel filter in any appropriate fashion. For example, the gripper may magnetically attach to the vessel filter. In one version, the gripper comprises a region configured to generate a powerful magnetic field to attach to a vessel filter. The gripper may also comprise a pneumatic gripper (e.g., drawing a vacuum to hold the vessel filter). In some versions, the gripper comprises an adhesive to chemically bond to a vessel filter. A gripper may also comprise any combination of these.

Detector

A detector may be linked to the gripper to detect the proximity of a vessel filter with respect to the removal device. In particular, a detector may indicate when a vessel filter is appropriately positioned so that the gripper may secure the vessel filter, allowing the vessel filter to be removed and repositioned by the removal device. Any appropriate detector may be used, including, electrical detectors, magnetic detectors, optical detectors, sonic detectors, pressure detectors, contact detectors, and the like. In some versions, the detector may detect proximity. For example, a detector may indicate how close a vessel filter is to the gripper of a removal device. In some versions, the detector may be a sensor to sense a condition related to the position (or proximity) of the vessel filter with respect to the removal device. For example, a sensor may detect pressure, fluid flow, light absorption, etc.

In general, a detector may determine when a vessel filter is positioned near enough to the gripper of the removal device so that the gripper may secure (e.g., grasp, hold or attach to) the vessel filter. In some versions, the detector continuously indicates how close the vessel filter is to the region of the removal device in which the gripper can effectively secure the vessel filter (e.g., by indicating the distance from the proper position). In some versions, the detector indicates only when the vessel filter is in an appropriate position for the grasper to secure the vessel filter.

The detector may be linked to the gripper. Generally, the detector may be linked to the gripper because the detector and the gripper are both located at the distal end of the removal device and both the detector and the grasper are part of the same removal device (e.g., physically linked). In some versions, the detector is connected directly to the gripper (e.g., a region of the gripper may be concurrent with the detector). In some versions, the detector is indirectly linked to the grasper. For example, a portion of the detector is connected to an elongate support body, and a portion of the gripper is also connected to the elongate support body. Generally, at least some portion of the detector is inserted into the lumen of a body vessel with the gripper when the removal device is used.

FIGS. 2A to 2D illustrate the general operation of a detector according to one embodiment of the present invention. In FIGS. 2A to 2D, the gripper region is shown in cross-section as a collapsible cone type of mechanical gripper. As described above, the collapsible cone comprises a plurality of gripper members (only two gripper members 201, 202 are shown in each of FIGS. 2A to 2D). The ends of the gripper members (e.g., the distal ends) are shown as having hooks 205, so that when the gripper is collapsed into a collapsed formation (not shown), the hooks may help to secure a portion of the vessel filter within the gripper (e.g., the collapsed cone). A vessel filter 210 is shown to the right of removal device 200.

Figure 2A:
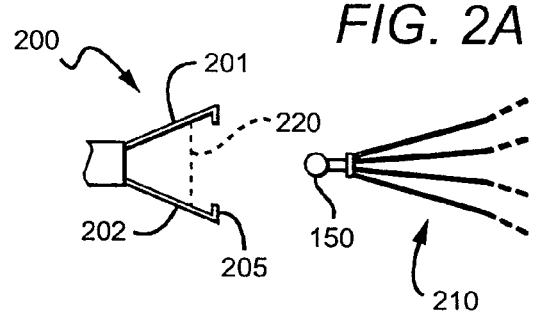
FIGS. 2A-2D illustrates detection of a vessel filter by a vessel filter removal or repositioning device according to the present invention.

In FIG. 2A, the removal device 200 is positioned too far from the vessel filter for the gripper of the removal device to effectively grip the vessel filter. The dashed line 220 across the mouth of the gripper (e.g., the collapsible cone-type gripper shown in cross-section) indicates a threshold for the gripper. When a portion of the vessel filter is located beyond this threshold 220, the gripper device will likely be able to grasp the vessel filter to secure it. A detector may indicate when the vessel filter has crossed this threshold. In some versions, a detector may also detect how far the vessel filter is from this threshold.

Figure 2B:
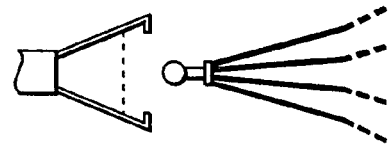
Figure 2C:
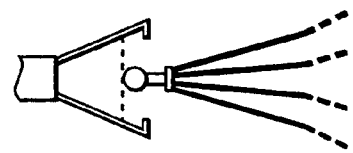

In FIG. 2B, the removal device has moved closer to the vessel filter. Thus, the hub portion of the vessel filter 150, is closer to the threshold 220, but is still too far for the grasper to able to secure the device. A detector would therefore not indicate that the vessel filter is positioned within the removal device; however, some versions of the detector may indicate that the vessel filter is approaching the threshold of the removal device. The removal device may be moved closer to the vessel filter, from the position in FIG. 2B, until at least a region of the filter device (e.g., the hub 150) has passed the threshold region, as shown in FIG. 2C. Once the vessel filter has passed the threshold 220 of the removal device, the detector indicates that the vessel filter is positioned within the active reach of the gripper, and thus that the gripper may secure the vessel filter.

Figure 2D:
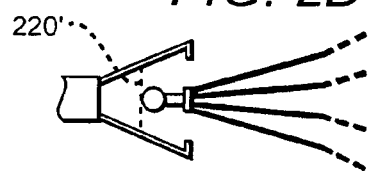

In some versions, the threshold may be set by the detector. However, the threshold may also be determined by the shape or size of the vessel filter. For example, if the gripper is configured to grip the legs of a vessel filter (e.g., the vessel filter shown in FIGS. 2A to 2D), the threshold 220' of the detector may be set so that it does not indicate that the vessel filter is in position until the legs are secured by the gripper, as shown in FIG. 2D. Thus, in FIG. 2D, the threshold is shown further in the cone, so that the hooks of the gripper members may grasp the legs when the gripper is engaged (e.g., collapsed).

The detector threshold may be just an imaginary threshold, indicating the effective range of the griper. However, the detector may be configured to change the threshold. For example, the sensitivity of the detector may be changed to adjust the threshold. In some versions, information from the detector is modified before any response or output is provided to reflect different thresholds (e.g., for different types of vessel filters, etc.). A detector may be configured in any appropriate way to permit accurate detection of a vessel filter. For example, the detector (or a portion of the detector) may be moved with respect to the gripper to change the threshold. In some versions, the detector is adjustable. In particular, the threshold (e.g., sensitivity, position, etc.) of the detector is adjustable.

Figure 3:
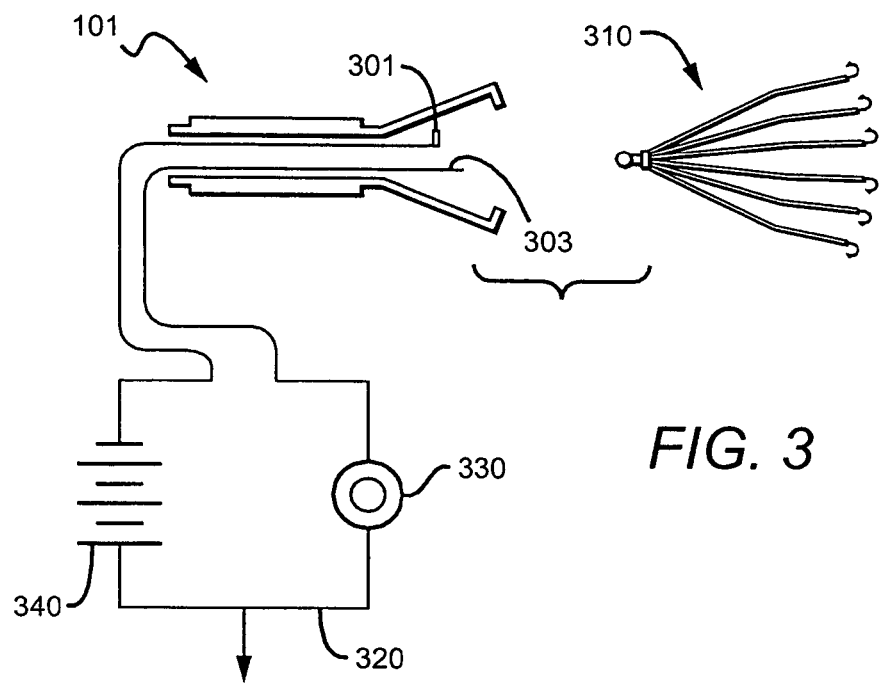
FIG. 3 shows a schematic of a vessel filter removal or repositioning device according to the present invention.

As described above, any appropriate detector may be used. FIG. 3 shows an example of an electrical detector. An electrical detector may comprise an electrical circuit that is open until a vessel filter closes the electrical circuit by contacting electrodes (e.g., a negative 301 and a positive 303 electrode) to close the circuit. Contact with an electrically conductive (e.g., metal) vessel filter permits electrical current to flow between the positive and the negative electrode, thereby activating an output device (such as an LED, buzzer, etc). In FIG. 3, the negative electrode 301 of the removal device detector is shown as a plate or disk near the center of the grasper (shown as a collapsible cone). This electrode may include a passage therethrough to pass an instrument, such as a guidewire. A positive electrode 303 is shown as a wire that also protrudes within the space formed by the cone of the gripper. When an electrically conductive vessel filter 310 contacts both the positive and negative terminals, the circuit 320 is complete (e.g., a closed loop) and current flows from a power source 340, between the terminals 301, 302 and the vessel filter 310, to the output 330 (e.g., an LED).

Figure 4A:
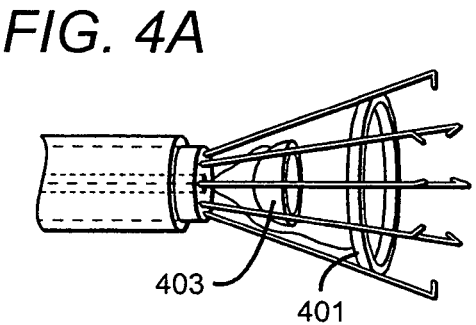
FIG. 4A shows a perspective view of the distal end of a vessel filter removal or repositioning device according to the present invention.
Figure 4B:
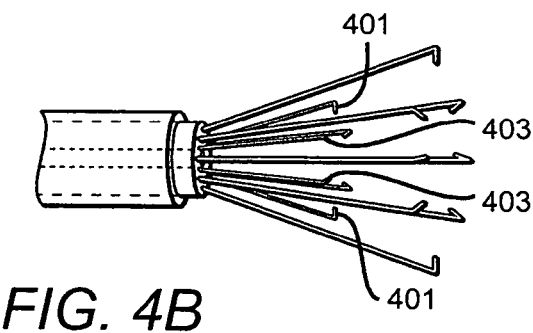
FIG. 4B shows a perspective view of the distal end of another vessel filter removal or repositioning device according to the present invention.

FIGS. 4A and 4B are additional examples of electrical detectors similar to the detector shown in FIG. 3. In FIGS. 4A and 4B, the positive and negative terminals are differently configured. For example, in FIG. 4A, the positive electrode 401 comprises a band of conductive material surrounding at least a portion of the inner wall of the cone. The negative electrode 403 is shown as a cup. Thus, if any portion of the vessel filter contacts both the inner wall of the gripper (cone) and the central cup 403, the detector will detect the vessel filter as positioned so that the gripper may secure the vessel filter. In FIG. 4B, the positive 401 and negative 403 electrodes are wires projecting into the cavity formed by the gripper (shown as a collapsible cone). As shown in FIG. 4B, a detector may comprise more than one positive and negative electrode. Also, one or more gripping members may be used as a positive or negative electrode.

In general, a detector (e.g., an electrical detector) may be in electrical connection with a power source (e.g., current source). Any appropriate power source may be used for the detector, including batteries, wall power, etc. The electrodes of the removal device may also be treated (e.g., coated) or may comprise a substance to enhance activity or to prevent damage to surrounding tissue. For example, the electrodes may be oxidized or chloridized, or may be treated to prevent substantial current flow through the surrounding liquid medium (i.e., blood). In some versions, the electrodes are connected to voltage or current limiters.

In some variations, the detector may be a thermocouple type detector. When two dissimilar metals are joined (e.g., contact), a voltage will may be generated related to the difference in temperature between a measuring junction and a reference junction (connection to the measuring device). Thus, a sensor may detect the voltage difference resulting when a portion of the detector (e.g., a contact) contacts the medical device (e.g., a vessel filter).

An electrical detector may also be configured as a mechanical (e.g., contact) detector requiring only contact with one portion of a vessel filter. For example, a positive and negative electrode may be separated from each other by a short distance, so that if the vessel filter contacts one of the electrodes, it displaces the electrode so that it contacts the other electrode, completing the circuit. Other types of electrical detectors may also be used. For example, the detector may detect contact with a vessel filter by a change in an electrical property of a portion of the gripper (e.g., a change in resistance, etc.). Other types of mechanical detectors may also be used. For example, a strain-gauge may be used to detect contact with a portion of the vessel filter.

Optical detectors (e.g., optical sensors) may also be used. For example, in one embodiment, an emitter/detector pair is placed near the gripper. In some versions, a detector may comprise a trigger, which is triggered by passage of a portion a vessel filter. For example, an optical detector may comprise an optical trigger that is set to detect an interruption of emitted or reflected light. Thus, a change in the detection of emitted light (e.g., infrared light) between the emitter/detector pair may indicate that a vessel filter is near the gripper. Other (non-optical) triggers may also be used, including physical triggers (e.g., tripwires, etc).

A detector may also be an electromagnetic detector. For example, the detector may detect electromagnetic energy (e.g., radio frequency (RF) or microwave energy). In some versions, the detectors may emit energy (e.g., RF or microwave) and detect electromagnetic properties induced in the vessel filter by the emission of energy. For example, a magnetic detector may be used to detect a vessel filter with respect to a gripper of a removal device. Any appropriate magnetic detector may be used. In one version, a magnetic detector comprises an emitter to emit a magnetic field that can induce a magnetic field in a vessel filter. The induced magnetic field is detected by a magnetic field receiver, or based on a change in the magnetic field that is emitted by the detector (e.g., polarization, phase shift, etc.).

In one version, a sonic (or vibratory) detector may detect sound reflectance off of a vessel filter as it nears the gripper of the removal device. Thus, a detector may also include an emitter (e.g., sonic emitter, light emitter, magnetic emitter, etc.). In some versions, the detector may detect changes in pressure due to the vessel filter nearing the gripper. In some versions, the detector is a signal sensor that detects a signal emitted by (or emanating from) a vessel filter. For example, a vessel filter may include a transmitter to transmit a signal.

Output

The detector may be connected to an output. The output may signal a user or the output may signal an electronic device. Any appropriate output may be used, including visual, electronic, aural, or tactile. In some versions, a user output is not provided, but the detector signals to a controller or other device that may automatically use the information (e.g., to activate the gripper).

Visual output may include lights (e.g., LEDs, etc.) and displays (e.g., monitors, etc.), which may be seen by a user (a user may be any person using the device, such as a doctor or other medical professional). In some versions, the output may be modified by additional hardware and/or software. For example, an output display may construct images of the removal device and vessel filter representing their positions relative to each other. In some versions, the output may be a simple "light/no light" to indicate when a vessel filter is or is not in position (e.g., past the threshold of the gripper) with respect to the removal device.

Aural output may include a buzzer, chime, or any other audible indicator. For example, an output may indicate by beat intensity or volume how near a vessel filter is to the threshold of a gripper. In some versions, a chime may indicate when the vessel filter is in position with respect to the removal devices.

The output may comprise a tactile output. For example, an output device may vibrate to indicate that a vessel filter is in position. In some versions, the output may be "force feedback," (e.g., inhibiting the advancement of the removal device in the direction of the vessel filter). The output may also comprise electronic output (e.g., signals to additional equipment, such as additional electronics, storage devices, controller, etc.). For example, the detector may send a signal to a controller or actuator for automating part of the removal procedure, as described further below. The output may include any combination of outputs (e.g., visual, tactile, etc.), as well.

Use of Removal Device

The removal devices described herein may be used to remove or reposition a vessel filter. A general method of removing or repositioning a vessel filter in an embodiment includes inserting a removal device into a body vessel containing a vessel filter and approaching the vessel filter with the removal device. The detector of the removal device is then used to determine when the vessel filter is positioned with respect to the removal device so that the removal device may grip the vessel filter. Thus, the removal device is advanced until the detector indicates (e.g., through an output such as an LED, monitor, speaker, vibration, or the like) that the gripper of the removal device is positioned to grip the vessel filter. The removal device may then grip the vessel filter with the gripper. The vessel filter can then be removed from the patient (e.g., after collapsing the vessel filter).

FIG. 5 illustrates one version of a removal device being used to remove a vessel filter 501. In this example, the vessel filter 501 is shown as a vessel filter having two baskets, which has been deployed within a body vessel (not shown) such as the vena cava. The removal device may be used to collapse and remove the vessel filter without significantly damaging the vessel (e.g., vessel walls).

In FIGS. 5A to 5E, a vessel filter 501 (such as a Recovery® Filter from Bard Peripheral Vascular, Inc.) has been implanted into a body vessel, such as the inferior vena cava. The vessel filter is typically oriented within the vessel so that the basket region 505 of the vessel filter 501 may act as a filter basket (e.g., for catching a thrombus clot). Thus, the hub portion 150 of the vessel filter 501 points in the direction of flow within the vessel (e.g., the direction of blood flow). The vessel filter 501 may be inserted into a subject and thereafter removed, either immediately, or at any appropriate time thereafter. For example, the vessel filter 501 may be removed, days, weeks, months, or even years after it has been implanted.

In this example, the vessel filter 501 has been implanted into the lumen of a subject's inferior vena cava (IVC). The vessel filter may be removed using a removal device as described herein. Access to the vessel filter within the IVC may be provided, for example, using a jugular approach, as is well known to one of skill in the art. A venipuncture (incision) is made at the appropriate location on a subject, after which a guidewire is advanced through the incision until reaching the approximate location of the vessel filter or at a location nearby. Because the removal device may be guided by a detector, the removal device can be positioned by the guidewire proximate to the vessel filter 501. The accessed vessel is then be dilated (e.g., with a 12 French dilator) to allow access by the removal device, after which an introducer catheter (e.g., a 10 French introducer catheter with a tapered dilator) is advanced over the guidewire and into the vein. In some versions, the introducer catheter has a radiopaque marker at the distal end to assist in visualization. The guidewire and the dilator are then removed, leaving the introducer catheter with a tip near the vessel filter. In some versions, the introducer catheter acts as an outer sleeve 135 of the gripper, keeping the gripper region of the removal device in a collapsed configuration until the gripper region (e.g., the collapsible cone region) exits the distal end of the introducer.

In FIG. 5A, a gripper having a collapsible cone 510 has been advanced through an introducer catheter 507 until the collapsible cone 510 has exited the introducer catheter and expanded, as shown. The gripper is positioned some distance from the vessel filter 501. In some versions, the detector of the removal device (linked to the gripper) indicates how far the gripper is from the vessel filter (e.g., how far the vessel filter is from the interior portion of the gripper cone). Thus, the removal device can be controllably advanced using the detector. When the detector indicates that the vessel filter (e.g., the hub or sleeve 150) is within an effective range for the gripper to grip the vessel filter, the gripper may be activated to secure the vessel filter. Thus, the removal device may be advanced as shown in FIG. 5B, until the detector indicates that at least a portion of the vessel filter may be gripped by the gripper.

As described above, an output (e.g., an LED) may be used to indicate to a user when the gripper region is in the correct position. Thus, the removal device may be precisely positioned without the aid of additional visualization techniques such as X-Ray, etc. FIG. 5C shows a cone type gripper that has been properly positioned over a vessel filter using a detector, and the gripper has secured the vessel filter by grasping the hub of the vessel filter. The cone is shown as collapsed over at least a part of the vessel filter (e.g., the hub). In this example, the cone is collapsed by moving the introducer catheter (outer sleeve) 507 over the cone region of the gripper, as indicated by the arrow 520. Once the gripper has secured the vessel filter, the removal device may be withdrawn, as shown in FIG. 5D, by withdrawing the gripper using the elongate support body to pull the gripper and the attached vessel filter into the introducer catheter (in the direction of the arrow 530). By pulling the gripper holding the vessel filter into the narrower-diameter introducer catheter, the vessel filter is collapsed, and may be safely withdrawn, as shown in FIG. 5E with the introducer catheter.

The methods and devices describe herein may be automated. For example, the removal device described herein may include one or more actuators to controllably move regions of the device. In one version, the device comprises an actuator to activate the gripper, to secure at least a portion of the vessel filter within the gripper. In some versions, the actuator controlling the gripper may be automated so that the gripper actives to secure the vessel filter once the detector detects that the vessel filter is properly positioned within the removal device. An actuator may also be used to withdraw (or collapse) the vessel filter. For example, an actuator may retract the gripper into a narrow-diameter tube (e.g., such as the introducer catheter as shown above for FIG. 5D). Thus, a controller may be used to coordinate the removal device described herein, including the gripper and the detector. A controller may comprise software, hardware, or any appropriate combination thereof.

The vessel filter removal or repositioning devices described herein may also be included as part of a kit. The kit may include additional materials appropriate for using the devices. For example, a kit may include instructions for using the devices. Instructions may be provided in any appropriate medium, including written, visual, pictographic, audible, or the like. In some versions, the instructions describe the methods of using the device as described above. Kits may also include additional materials (e.g., introducers, guidewires, sheaths, etc.) useful in conjunction with the devices described herein.

While the invention has been described in terms of particular variations and illustrative figures, those of skill in the art will recognize that the invention is not limited to the variations or figures described. In addition, where methods and steps described above indicate certain events occurring in certain order, those of skill in the art will recognize that the ordering of certain steps may be modified and that such modifications are in accordance with the variations of the invention. Additionally, certain steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. A vessel filter removal or repositioning device, comprising:
    an elongate support body having a central longitudinal axis;
    a collapsible cone gripper attached to the distal end of the support body, wherein the cone is configured to translate from an expanded configuration to a retracted configuration within a body vessel;
    a detector, positioned within a conical area defined by the gripper, to detect the proximity of a vessel filter to the gripper, the detector including a positive electrode and a negative electrode, wherein an electrical circuit is completed upon contact between the vessel filter and both the positive electrode and negative electrode; and
    an output signal generated by the detector upon completion of the electrical circuit, the output signal indicating that the vessel filter is in a position to be gripped by the collapsible cone gripper.

2. The device according to claim 1, wherein the output signal comprises an LED.

3. A vessel filter removal or repositioning device, the device comprising:
    an elongate support body having a central longitudinal axis;
    a plurality of gripping members at the distal end of the elongate support body extending therefrom, the gripping members being convertible between an expanded funnel-shaped configuration, in which the gripping members extend away from the central longitudinal axis, and a retracted configuration, in which the gripping members converge toward the central longitudinal axis;
    a flexible liner connected to the gripping members forming an inner surface; and
    a positive electrode and a negative electrode, each in electrical connection to an output, the output indicating when a vessel filter contacts the positive and negative electrodes, completing an electrical circuit between the positive and negative electrodes, wherein the positive and negative electrodes are treated to prevent substantial current flow through the blood surrounding the vessel filter.

4. The device according to claim 3, wherein the output comprises an LED.

5. The device according to claim 3, wherein at least one of the gripping members comprises a hook member formed from an elongate metallic material.

6. The device according to claim 3, wherein at least one of the gripping members comprises the positive or negative electrode.

7. The device according to claim 3, wherein either the positive or negative electrode comprises a wire surrounded by the gripping members.

8. The device according to claim 3, wherein the positive electrode comprises a loop of electrically conductive material encircling the central longitudinal axis.

9. The device according to claim 3, wherein the negative electrode comprises a cup region surrounded by the gripping members.

10. The device according to claim 3, further comprising a battery in electrical contact with the positive and negative electrodes.

11. A kit for repositioning or removing a vessel filter, comprising:
    the vessel filter removal or repositioning device of claim 3; and
    instructions for using the vessel filter removal or repositioning device to remove or to reposition a vessel filter.

12. A method of repositioning or removing a vessel filter, comprising:

inserting a vessel filter removal or repositioning device into a body vessel containing a vessel filter, said vessel filter removal or repositioning device comprising:
- a gripper to remove or reposition a vessel filter from a body vessel;
- a detector linked to the gripper to detect the proximity of a vessel filter to the gripper, the detector including a positive electrode and a negative electrode, wherein an electrical circuit is completed upon contact between the vessel filter and both the positive electrode and negative electrode; and
- an output to indicate a signal from the detector upon completion of the electrical circuit, the output signal indicating that the vessel filter is in a position to be gripped;

approaching the vessel filter within the body vessel with the vessel filter removal or repositioning device;

detecting the vessel filter with the vessel filter removal or repositioning device; and gripping the vessel filter with the vessel filter removal or repositioning device.

\* \* \* \* \*